US008753515B2

(12) United States Patent
Curtis et al.

(10) Patent No.: US 8,753,515 B2
(45) Date of Patent: Jun. 17, 2014

(54) DIALYSIS SYSTEM WITH ULTRAFILTRATION CONTROL

(75) Inventors: James R. Curtis, Portland, OR (US);
Ladislaus F. Nonn, Portland, OR (US);
Julie Wrazel, Portland, OR (US)

(73) Assignee: Home Dialysis Plus, Ltd., Sunnyvale, CA (US)

( * ) Notice: Subject to any disclaimer, the term of this patent is extended or adjusted under 35 U.S.C. 154(b) by 402 days.

(21) Appl. No.: 12/795,498

(22) Filed: Jun. 7, 2010

(65) Prior Publication Data

US 2011/0132838 A1     Jun. 9, 2011

(51) Int. Cl.
*B01D 61/32* (2006.01)
*B01D 61/14* (2006.01)
*B01D 61/24* (2006.01)
*A61M 1/14* (2006.01)
*A61M 1/34* (2006.01)

(52) U.S. Cl.
USPC ........... 210/646; 210/650; 210/739; 210/741; 604/4.01; 604/5.01; 604/5.04; 604/6.1; 604/6.11; 604/28

(58) Field of Classification Search
CPC .............. A61M 1/342; A61M 1/3621; A61M 2205/3331; A61M 2205/3344; B01D 1/145; B01D 61/22
USPC ............. 210/645, 646, 650, 739, 741, 85, 87, 210/90, 97, 102, 103, 134, 143, 321.65; 604/4.01, 5.01, 5.04, 6.1, 6.11, 28
See application file for complete search history.

(56) References Cited

U.S. PATENT DOCUMENTS

| | | | |
|---|---|---|---|
| 4,229,299 A | 10/1980 | Savitz et al. | |
| 4,317,725 A | 3/1982 | Kume et al. | |
| 5,645,734 A | 7/1997 | Kenley et al. | |
| 5,744,031 A * | 4/1998 | Bene ........................ | 210/321.71 |
| 5,788,099 A | 8/1998 | Treu et al. | |
| 5,879,316 A | 3/1999 | Safar et al. | |
| 6,325,774 B1 * | 12/2001 | Bene et al. .................... | 604/4.01 |
| 6,530,252 B1 | 3/2003 | Esser | |
| 6,530,262 B1 | 3/2003 | Esser | |
| 6,672,502 B1 | 1/2004 | Paul et al. | |
| 6,730,233 B2 * | 5/2004 | Pedrazzi ....................... | 210/739 |

(Continued)

FOREIGN PATENT DOCUMENTS

| | | |
|---|---|---|
| DE | 8702995 | 5/1987 |
| EP | 0165751 | 12/1985 |

(Continued)

OTHER PUBLICATIONS

German Patents Fulltext file with English machine translation for publication No. DE8702995, published May 7, 1987, entitled, No Name Given.

*Primary Examiner* — John Kim
(74) *Attorney, Agent, or Firm* — Fred C. Hernandez; Mintz Levin Cohn Ferris Glovsky and Popeo, P.C.

(57) ABSTRACT

Systems and methods are disclosed for performing hemodialysis that include fluid handling systems that provide accurate control over the type and level of hemodialysis being performed. The system includes a first pump for pumping dialysate into a dialyzer and a second pump for pumping dialysate out of the dialyzer. The system also includes a third pump that provides improved control of a level of ultrafiltration, hemodiafiltration, or both.

22 Claims, 6 Drawing Sheets

(56) References Cited

U.S. PATENT DOCUMENTS

| | | |
|---|---|---|
| 6,793,831 B1 | 9/2004 | Paul et al. |
| 7,131,956 B1 * | 11/2006 | Pirazzoli et al. ............ 604/6.09 |
| 2007/0029365 A1 | 2/2007 | Paul et al. |
| 2008/0108122 A1 | 5/2008 | Paul et al. |
| 2009/0101549 A1 | 4/2009 | Kamen et al. |
| 2010/0271296 A1 | 10/2010 | Kopychev et al. |
| 2010/0326914 A1 | 12/2010 | Drost et al. |
| 2010/0326916 A1 | 12/2010 | Wrazel et al. |
| 2011/0300230 A1 | 12/2011 | Peterson et al. |

FOREIGN PATENT DOCUMENTS

| | | |
|---|---|---|
| EP | 0679100 | 11/1995 |
| EP | 0796997 | 9/1997 |
| WO | WO 00-16916 | 3/2000 |
| WO | WO 2007-126360 | 11/2007 |
| WO | WO2010-062698 | 6/2010 |
| WO | WO 2010-151419 | 12/2010 |

* cited by examiner

Figure 6

DIALYSIS SYSTEM WITH ULTRAFILTRATION CONTROL

REFERENCE TO PRIORITY DOCUMENT

This application claims priority of U.S. Provisional Patent Application Ser. No. 61/267,043, filed Dec. 5, 2009. Priority of the aforementioned filing date is hereby claimed and the disclosure of the Provisional Patent Application is hereby incorporated by reference in its entirety.

BACKGROUND

Chronic dialysis has been performed on patients with kidney failure since the early 1960's. A dialyzer is a device for cleansing blood through hemodialysis by a process of diffusion and/or convection of waste products, dissolved solutes and fluid from the blood across a semi permeable membrane into a dialysis solution known as dialysate. A dialysis system is an assembly that includes the dialyzer and associated equipment to support the dialyzer, such a plumbing and pumps.

Diffusion is the principal mechanism in which dialysis removes waste products such as urea, creatinine, phosphate and uric acid, among others, from the blood. A differential between the chemical composition of the dialysate and the chemical composition of the blood causes the waste products to be drawn through the semi-permeable membrane from the blood into the dialysate. Ultrafiltration is a process in dialysis where fluid is caused to move across the membrane from the blood into the dialysate for the purpose of removing excess fluid from the patient's blood stream. Along with water, some solutes are also drawn across via convection rather than diffusion. Ultrafiltration is a result of a pressure differential between the blood compartment of the dialyzer and the dialysate compartment of the dialyzer where fluid will move from a higher pressure to a lower pressure. In some circumstances, by design or unintentionally, fluid in the dialysate compartment is higher than the blood compartment, causing fluid to move from the dialysate compartment into the blood compartment. This is commonly referred to as reverse ultrafiltration.

It would be convenient for a patient to be able to perform dialysis in his or her home. Unfortunately, current dialysis systems are large in size, making them generally unsuitable for use in a patient's home. Current dialysis systems are also energy-inefficient in that they use large amounts of energy and require enormous amounts of water for proper use. Although some home dialysis systems are available, they generally use complex flow-balancing technology that is relatively expensive to manufacture and most systems are designed with a system of solenoid valves that create high noise levels. As a result, most dialysis treatments are performed at dialysis centers.

SUMMARY

In view of the foregoing, there is a need for improved dialysis systems that are smaller, more portable, consume less water and that provide precise control over a level of ultrafiltration. Disclosed are systems and methods for performing hemodialysis that include fluid handling systems and provide accurate control over the type and level of hemodialysis being performed. The system includes a first pump for pumping dialysate into a dialyzer and a second pump for pumping dialysate out of the dialyzer. The system also includes a third pump that provides improved control of a level of ultrafiltration, hemodiafiltration, or both, as described in detail below.

In one aspect, there is disclosed a method of performing dialysis, comprising: operating a first pump to pump dialysate at a first flow rate through a fluid inlet pathway into a dialyzer; operating a second pump to pump the dialysate through a fluid outlet pathway out of the dialyzer; operating a third pump to pump the dialysate through the fluid outlet pathway in cooperation with the second pump, wherein the second and third pumps cooperate to collectively achieve a second flow rate through the fluid outlet pathway from the dialyzer; and pumping blood through the dialyzer in communication with the dialysate such that the dialyzer dialyzes the blood.

In another aspect, there is disclosed a method of performing dialysis, comprising: providing a dialysis system having an inlet conduit through which fluid flows in an inward direction toward a dialyzer and an outlet conduit through which fluid flows in an outward direction from the dialyzer; pumping fluid through the inlet conduit using a first pump; pumping fluid through the outlet conduit using a second pump; and using a third pump to supplement the pumping of the second pump through the outlet conduit.

In another aspect, there is disclosed a dialysis system, comprising: a dialyzer having a blood flow pathway through which blood flows; a fluid inlet pathway configured to provide incoming fluid to the dialyzer; a fluid outlet pathway configured to receive outgoing fluid from the dialyzer; a first pump coupled to the fluid inlet pathway and configured to pump the fluid through the fluid inlet pathway toward the dialyzer; a second pump coupled to the fluid outlet pathway and configured to pump the fluid through the fluid outlet pathway away from the dialyzer; and a third pump coupled to the fluid outlet pathway, the third pump configured to work in cooperation with the second pump to achieve a desired flow rate of fluid to or from the blood flowing through the dialyzer.

Other features and advantages should be apparent from the following description of various embodiments, which illustrate, by way of example, the principles of the disclosed devices and methods.

DETAILED DESCRIPTION

In order to promote an understanding of the principals of the disclosure, reference is made to the drawings and the embodiments illustrated therein. Nevertheless, it will be understood that the drawings are illustrative and no limitation of the scope of the disclosure is thereby intended. Any such alterations and further modifications in the illustrated embodiments, and any such further applications of the principles of the disclosure as illustrated herein are contemplated as would normally occur to one of ordinary skill in the art.

Figure 1A:
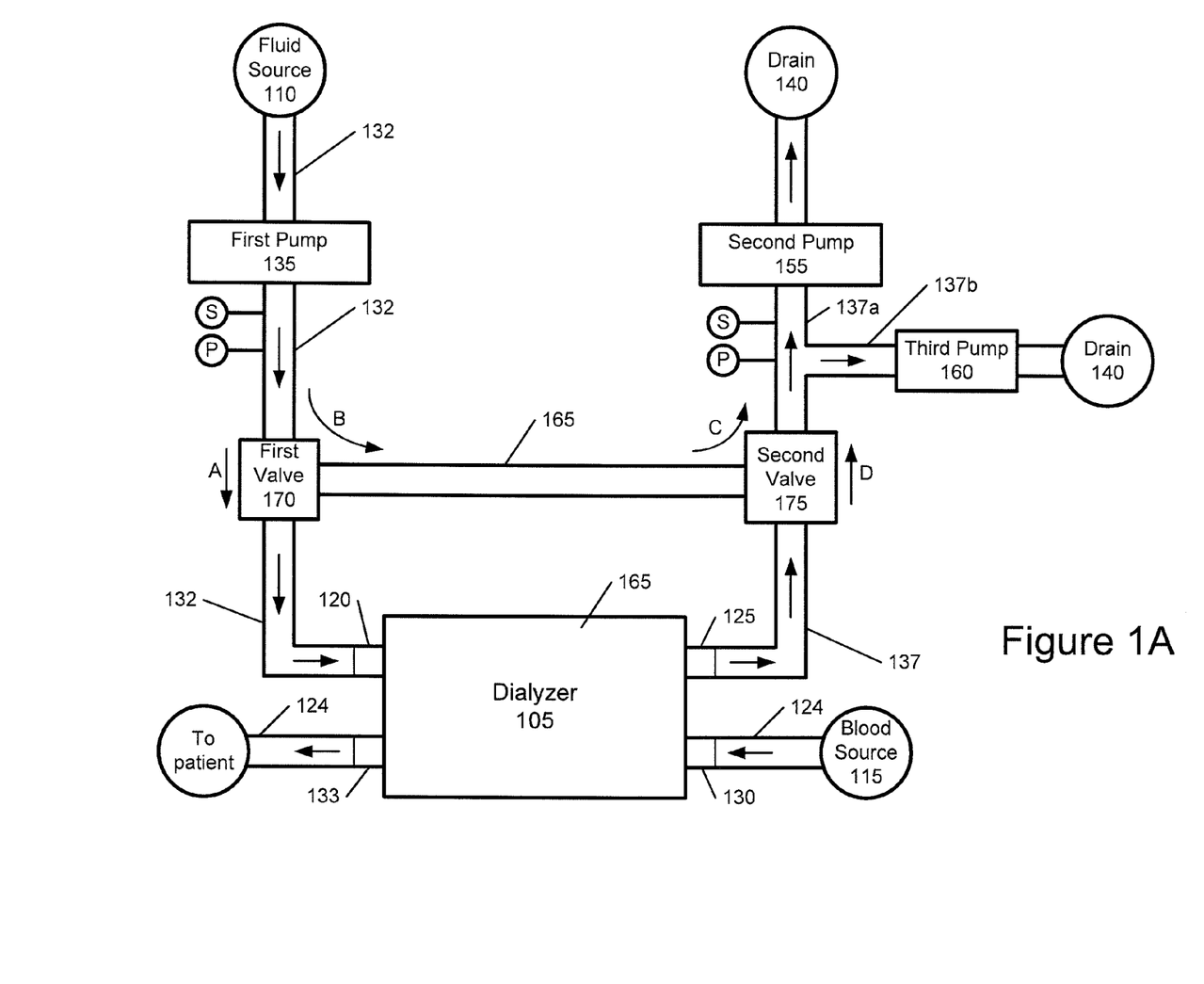
FIG. 1A shows a schematic view of a dialysis system adapted to perform dialysis of a patient's blood.

FIG. 1A shows a schematic view of a dialysis system adapted to perform hemodialysis of a patient's blood. The system includes an arrangement of three or more pumps that provide improved control over the type of hemodialysis being performed. By varying the relative pump speeds of the three pumps, an operator can vary the level of blood filtration and can also selectively achieve ultrafiltration and hemodiafiltration of the blood.

Ultrafiltration is a process in dialysis where fluid is caused to move across a dialyzer membrane via diffusion from the blood into the dialysate for the purpose of removing excess fluid from the patient's blood stream. Along with water, some solutes are also drawn across the membrane via convection rather than diffusion. Ultrafiltration is a result of a pressure differential between the blood compartment and the dialysate compartment where fluid will move from a higher pressure to a lower pressure.

In some circumstances, by design or unintentional, fluid in the dialysate compartment is higher than the blood compartment causing fluid to move from the dialysate compartment into the blood compartment. This is commonly referred to as reverse ultrafiltration.

In hemodiafiltration a high level of ultrafiltration is created, greater than the amount required to remove fluid from the patient's blood, for the purpose of increasing convective solute transport across the membrane. The amount of fluid in excess of what is required to be removed from the patient's blood must therefore be returned to the blood stream in order to avoid an adverse blood reaction. This is accomplished by intentionally increasing the pressure in the dialysate compartment of the dialyzer to cause the appropriate amount of reverse ultrafiltration. This process of ultrafiltration alternating with reverse ultrafiltration is often referred to as "push-pull hemodiafiltration". This is a significant improvement over more common methods of hemodiafiltration where sterile fluid is administered to the patient in a location outside of the dialyzer.

The dialysis system includes a dialyzer 105 that is fluidly connected to a source 110 of fluid (such as dialysate) and also to a source 115 of blood to be dialyzed. The source 115 of blood may be a patient. The source 110 of fluid may be a dialysate preparation system that prepares dialysate for use in the dialysis system. The dialysate preparation system may include a water purification system that purifies water pursuant to systems and methods described in co-pending U.S. patent application Ser. No. 12/795,382, entitled "Fluid Purification System", which is filed concurrently herewith and which is incorporated by reference in its entirety. In addition, the dialyzer 105 may be at least partially configured with microfluidic pathways as described in co-pending U.S. patent application Ser. No. 12/795,371, entitled "Microfluidic Devices", filed concurrently herewith, which claims priority to U.S. Provisional Application Ser. No. 61/220,117, filed on Jun. 24, 2009, which applications are incorporated by reference in their entirety. U.S. patent application Ser. No. 12/795,444, entitled "Dialysis System", filed concurrently herewith, is also incorporated by reference in its entirety. Dialysate flows into the dialyzer 105 through a fluid inlet 120 and out of the dialyzer 105 through a fluid outlet 125. Blood flows through the dialyzer 105 via a blood flow pathway 124 that includes a blood inlet 130 into the dialyzer 105 and a blood outlet 133 out of the dialyzer. From the dialyzer 105, the blood flows back to the patient. The dialyzer 105 is described in more detail below.

The dialysis system includes plumbing that forms a plurality of fluid flow pathways, which may be any type of conduit through which a fluid such as dialysate may flow. The fluid flow pathways include an inlet pathway 132 through which a fluid such as unused dialysate flows from the source 110 toward and into the dialyzer 105. At least a first pump 135 is positioned along or in communication with the inlet pathway 132 for pumping the fluid toward the dialyzer 105 at a desired flow rate. One or more sensors S may be coupled to the fluid flow pathway for sensing one or more characteristics of the incoming fluid, such as pressure, flow rate, temperature, conductivity, etc. In addition, one or more sample ports P may be coupled to the fluid flow pathways that provide access to fluid flowing through the piping. FIG. 1 shows the sensors S and sample ports P coupled to the fluid flow pathways at specific locations, although the quantity and locations of the sensors S and sample ports P may vary.

The fluid flow pathways further include an outlet pathway 137 through which used dialysate flows out of the dialyzer 105 toward one or more drains 140. In some embodiments, the dialysate exiting the dialyzer may be used to pre-heat other incoming fluids in the system, such as the water stream entering the heat exchange and purification system, before reaching the drain 140. The outlet pathway 137 bifurcates into two or more outlet pathways including a main outlet pathway 137a and a secondary outlet pathway 1137b. At least a second pump 155 is positioned along or in communication with the main outlet pathway 137a for pumping the dialysate out of and away from the dialyzer 105 through the main outlet pathway 137a.

A third pump 160 is positioned along or in communication with the secondary outlet pathway 137b. The third pump 160 can be used to augment fluid flow through the fluid flow pathways such as to selectively achieve differentials in flow rates between the inflow pathway 132 and the outflow pathway 132 pursuant to achieving various types of dialysis, including hemodialysis, ultrafiltration, and hemodiafiltration, as described more fully below. The third pump pumps dialysate through the fluid flow pathways when the system is in dialysis mode. The third pump may also pump another fluid, such as water or disinfectant, when the system is in a different mode, such as in a calibration mode or in a cleaning mode. The third pump 160 can also be used to calibrate flow rates between the first pump 135 and the second pump 155, as described more fully below.

Figure 1B:
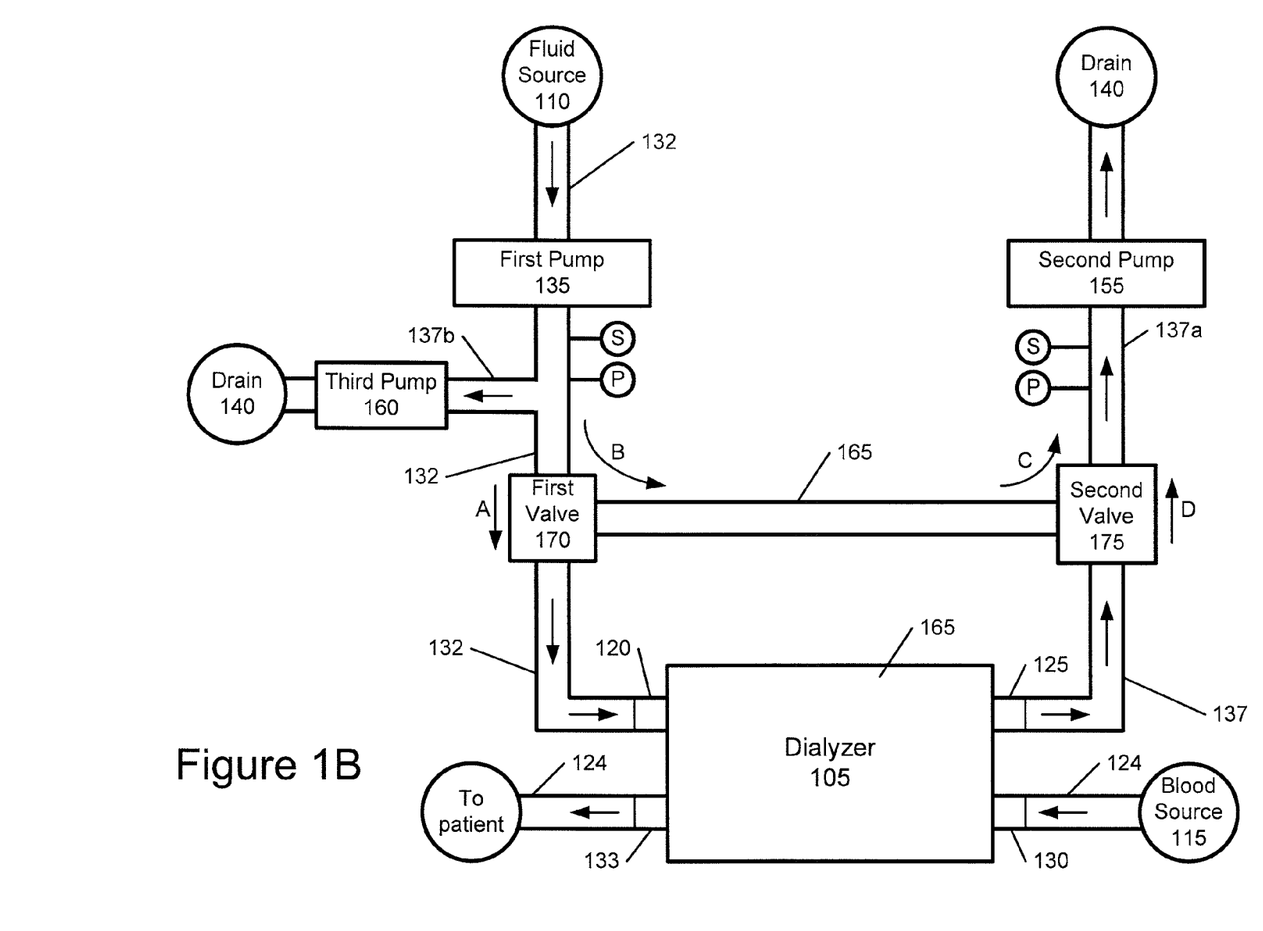
FIG. 1B shows a schematic view of another embodiment of a dialysis system.

In another embodiment, shown in FIG. 1B, the third pump 160 is positioned along the inflow pathway 132 upstream of the inlet 120 of the dialyzer 105. In this embodiment, the secondary outlet pathway 137 branches off the inlet pathway 132 at a location downstream of the first pump 135 and upstream of the first valve 170. The third pump 160 pumps fluid toward the drain 140. The embodiment of FIG. 1A may be more efficient than the embodiment of FIG. 1B because the third pump 160 in FIG. 1B pumps fresh, unused dialysate into the drain 140 while the third pump in FIG. 1A pumps used dialysate into the drain 140. In another embodiment, the third pump 160 and the second pump 155 are both positioned along a single, non-bifurcating outflow pathway.

Various types of pumps may be used for the first, second and third pumps. In an embodiment, the pumps are nutating pumps. On other embodiments, the pumps could be rotary lobe pumps, progressing cavity pumps, rotary gear pumps, piston pumps, diaphragm pumps, screw pumps, gear pumps, hydraulic pumps, vane pumps, regenerative (peripheral) pumps, or peristaltic pumps, or any combination thereof. Other types of pumps can also be used. The first pump 135 and the second pump 155 may be driven by a common shaft to ensure synchrony of the pump strokes and the volume of fluid pumped. It is understood that first pump 135 and the second pump 155 may also be fully independent from each other.

As mentioned, any of a variety of fluid conduits may be used to form the fluid flow pathways. In an embodiment, at least a portion of the fluid flow pathway is formed of piping having an inside diameter from ⅛ inch to ½ inch. The flow rate in the piping could range between about 50 ml/min to about 1,000 ml/min. In an embodiment, the flow rate is in the range of between about 100 ml/min and about 300 ml/min.

With reference again to FIG. 1A, the fluid flow pathways further include a bypass pathway 165 that fluidly directly connects the inlet pathway 132 and the outlet pathway 137. An exemplary purpose of the bypass pathway 165 is to provide a fluid flow pathway where fluid can flow into and out of the dialysis system and bypass the dialyzer 105, such as for flushing, cleaning or calibrating the system. In an embodiment, the junction between the inlet pathway 132 and bypass pathway 165 is located upstream of the fluid inlet 120 of the dialyzer 105, and the junction between the bypass pathway 165 and the outlet pathway is located downstream of the fluid outlet 125 of the dialyzer 105. However, other configurations of the bypass pathway 165 can be used to achieve bypassing of the dialyzer 105.

A first valve 170 is positioned at the junction between the inlet pathway 132 and the bypass pathway 165. A second valve 175 is positioned at the junction between the bypass pathway 165 and the outlet pathway 137. The first valve 170 and second valve 175 are three-way valves, such as solenoid valves, that can be used to selectively regulate fluid flow through the fluid flow pathways. That is, the first valve 170 can be set to either of two or more settings including (1) a dialysis setting wherein the first valve directs all incoming fluid along the inlet pathway 132 toward the dialyzer 105 (as represented by arrow A in FIG. 1) and prevents incoming fluid from flowing into the bypass pathway 165; or (2) a bypass setting wherein the first valve 170 diverts all the incoming fluid into the bypass pathway 165 (as represented by arrow B in FIG. 1) and the prevents incoming fluid from flowing past the first valve toward the dialyzer 105.

The second valve 175 can also be set to either of two settings including (1) a bypass setting wherein the second valve 175 directs incoming fluid from the bypass pathway 165 into the outlet pathway 137 (as represented by arrow C in FIG. 1); or (2) a dialysis setting wherein the second valve 175 closes flow from the bypass valve 165 such that outgoing fluid from the dialyzer outlet 125 continues to flow outward along the outlet pathway 137 (as represented by arrow D in FIG. 1.) The first valve 175 and the second valve 160 are generally both set in tandem to either the bypass setting or the dialysis setting. The system may include a control and safety system that ensures that the first and second valves are not set to incompatible settings.

The arrangement of the various components of the dialysis system shown in FIGS. 1A and 1B are exemplary and other arrangements are possible. For example, the flow pathways and the pumps may be placed in different locations along the flow pathways from what is shown in FIG. 1. In an embodiment, the third pump 160 is positioned in the flow pathway at a location upstream of the dialyzer 105 and downstream of the first valve 170 or the third pump can be positioned downstream of the dialyzer 105 and upstream of the second valve 175. Moreover, the system can employ more than three pumps.

Dialyzer and Various Forms of Dialysis

Figure 2:
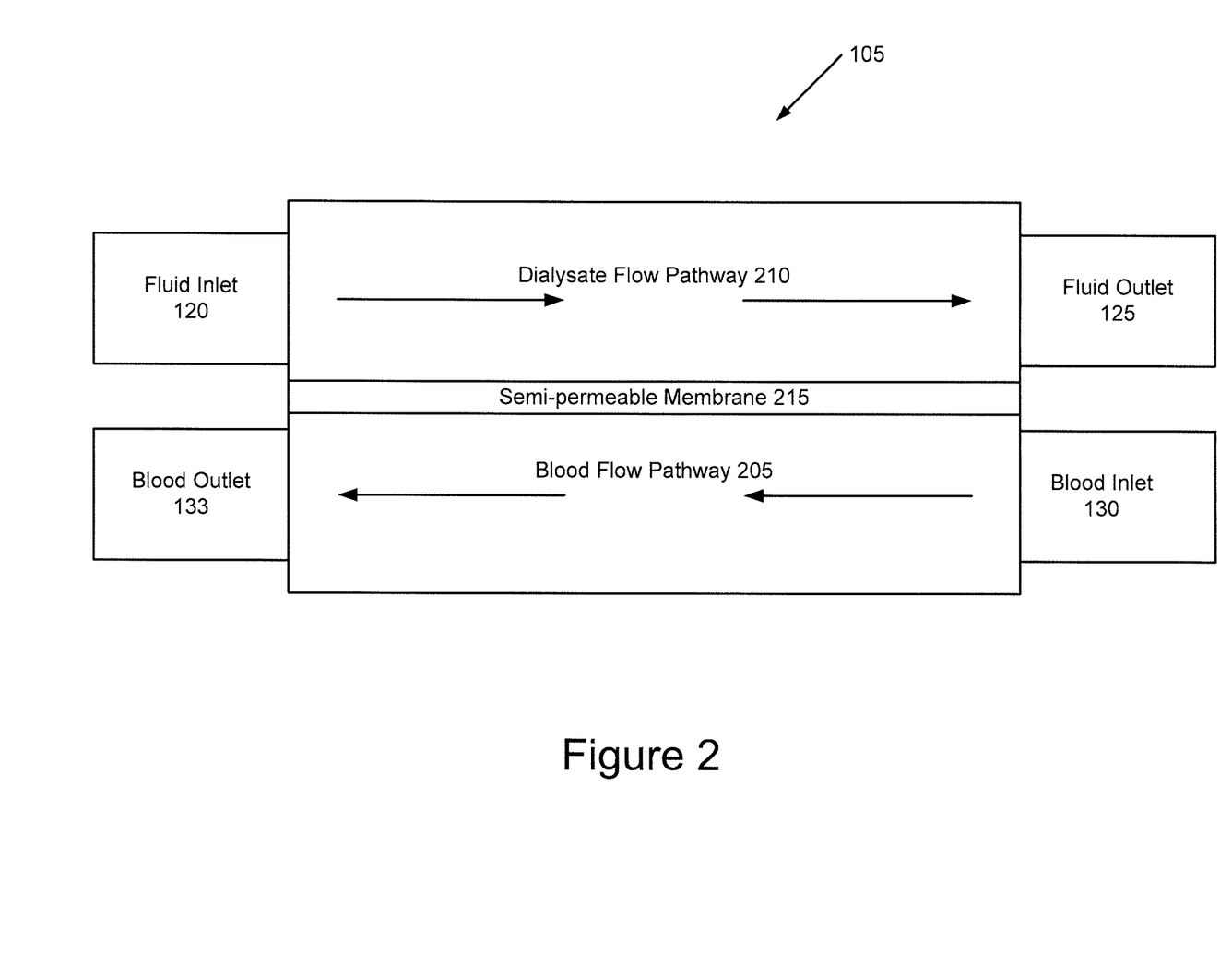
FIG. 2 is a schematic view of a dialyzer of the dialysis system.

FIG. 2 is a schematic, cross-sectional view of the dialyzer 105, which defines a blood compartment having a blood flow pathway 205 and a dialysate compartment having a dialysate flow pathway 210 separated by a semi-permeable membrane 215. The blood (from a patient) enters the blood flow pathway 205 via the blood inlet 130, flows through the blood flow pathway 205, and exits via the blood outlet 133. The dialysate enters the dialysate flow pathway 210 via the fluid inlet 120, flows through the dialysate flow pathway 210, and exits via the fluid outlet 125. The semi-permeable membrane 215 is configured to allow the transfer of one or more substances from the blood in the blood flow pathway 205 to the dialysate in the dialysate flow pathway 210, or visa-versa. Some examples of materials that may be used as the semipermeable membrane 215 include polymers, copolymers, metals, ceramics, composites, and/or liquid membranes. One example of a composite membrane is polysulfone-nanocrystalline cellulose composite membrane such as AN69 flat sheet membranes available from Gambro Medical. Gas-liquid contactor membranes may also be employed for transferring a substance between a liquid and gas such as for oxygenation of blood, whereby the membrane allows transfer of carbon dioxide and oxygen, such that oxygen transfers to blood from oxygen or oxygen-enriched air, and carbon dioxide transfers from the blood to the gas. Fluid membranes may also be employed. Fluid membranes comprise a lamina having through cut microchannels containing fluid and a first and second membrane support positioned to contain fluid in the microchannels.

When flowing through the dialyzer 105, the blood and the dialysate may flow in a counter-flow configuration wherein blood flows through the blood flow pathway 205 in one direction and the dialysate flows through the dialysate flow pathway 210 in the opposite direction. The dialyzer 105 is described in the context of having a counter-flow configuration although a cross-flow configuration may also be used. As the blood and water flow along the membrane 215, hemodialysis occurs. That is, waste solutes move across the semipermeable membrane 215 from the blood into the dialysate via diffusion as a result of the differential of solute concentration between the blood and the dialysate. The flow of the blood and dialysate, which may be counter-, cross- or concurrent-flow, maintains the concentration gradient of solutes between the blood and dialysate, which helps to remove more urea and creatinine from the blood. The concentrations of solutes (for example potassium, phosphorus, and urea) may be undesirably high in the blood, but low or absent in the dialysate and constant replacement of the dialysate ensures that the concentration of undesired solutes is kept low on the dialysate side of the membrane. The dialysate has levels of minerals like potassium and calcium that are similar to their natural concentration in healthy blood. For another solute, bicarbonate, the dialysate level is set at a slightly higher level than in normal blood, to encourage diffusion of bicarbonate into the blood, to maintain a patient's CO2 level, and act as a pH buffer to neutralize the metabolic acidosis that is often present in these patients.

The dialyzer 105 is also configured to perform ultrafiltration wherein a pressure differential across the membrane 215 results in fluid and dissolved solutes passing across the membrane 215 from the blood to the dialysate.

The dialyzer 105 is also configured to perform hemodiafiltration wherein solute movement across the semipermeable membrane 215 is governed by convection rather than by diffusion. A positive hydrostatic pressure differential between the blood flow pathway 205 and the dialysate flow pathway 210 drives water and solutes across the semipermeable membrane 215 from the blood flow pathway to the fluid flow pathway. Solutes of both small and large molecules get dragged through the semipermeable membrane 215 along with the fluid. In a typical hemodiafiltration procedure, the direction of water and solute movement is oscillated between moving water and solutes from the blood into the dialysate and moving water and solutes from the dialysate into the blood. Over a predetermined span of time, there is a net zero loss and zero net gain of fluid from the blood into the dialysate. However, during discrete time periods within that span of time, there can be a net loss of fluid from the blood into the dialysate and a net gain of fluid into the blood from the dialysate.

Operation of Pumps to Achieve Hemodialysis without Ultrafiltration

With reference again to FIG. 1A, the dialysis system achieves hemodialysis without ultrafiltration when the flow rate through the inlet pathway 132 is equal to or substantially equal to the flow rate through the outlet pathway 137. In other words, hemodialysis without ultrafiltration is achieved where the amount of dialysate flowing into dialyzer 105 via the inlet pathway 137 is substantially equal to the amount of dialysate flowing out of the dialyzer via the outlet pathway 137 over a period time. This can be achieved by operating the first pump 135 at a first pump rate to provide a first flow rate through the inlet pathway 132 and operating the second pump 155 and the third pump 160 at respective pump rates that collectively achieve a flow rate through the outlet pathway 137 that is equal to the flow rate through the inlet pathway 132.

In an embodiment, the system performs a hemodialysis procedure utilizing all three pumps in an active state substantially continuously throughout the hemodialysis procedure. The system adjusts the pump rate of the third pump 160 to achieve a desired balance of equal flow rates between the inlet pathway 132 and the outlet pathway 137. In this embodiment, the first pump 135, second pump 155, and third pump 160 are all active throughout the hemodialysis procedure with the first and second pumps operating at different pump rates and the third pump operating at a pump rate that achieves a balanced flow rate between the inlet pathway 132 and the outlet pathway 136. The third pump is typically operated at a pump rate that is equal to the differential between the pump rate of the first pump and the pump rate of the second pump. In this manner, the second and third pumps collectively achieve a flow rate through the outlet pathway 137 that is equal to the flow rate through the inlet pathway 132.

For example, to achieve a desired flow rate of, for example, 100 ml/min through the dialyzer, the first pump 135 is set to provide a flow rate of 100 ml/min through the inlet pathway 132 and the second pump 155 is deliberately set out of balance with the first pump 135, to provide, for example, a flow rate of only 80 ml/min. This would provide a flow rate differential of 20 ml/min between the first pump and the second pump. The pump rate of third pump 160 is set to provide a flow rate of 20 ml/min, which is equal to the differential between the flow rates of the first and second pumps. In this manner, the second pump 155 and the third pump 160 collectively achieve a flow rate of 100 ml/min through the outlet pathway 137 which is equal to the flow rate of through the inlet pathway 132 such that the flow rates are balanced across the dialyzer. Under such conditions, waste solutes move across the dialyzer's semipermeable membrane from the blood stream into the dialysate via diffusion to perform hemodialysis.

The flow rates through the inlet pathway 132 and the outlet pathway 137 may be measured using one or more of the sensors S. In an embodiment, the sensors are flow rate sensors that directly measure flow rates through the inlet pathway 132 and outlet pathway 137. In another embodiment, the sensors are pressure sensors that provide indications as to the fluid pressure within the inlet pathway 132 and the fluid pressure within the outlet pathway 137. Fluid pressure is a function of the flow rate through the flow pathways and therefore provides an indirect measurement of flow rate. Where the fluid pressure in the inlet pathway 132 is equal to the fluid pressure in the outlet pathway 137, this is an indication that the flow rates are balanced between the inlet pathway and outlet pathway. Where the fluid pressure in the inlet pathway 132 is less than the fluid pressure through the outlet pathway 137, this is an indication that the flow rate through the inlet pathway 132 is less than the flow rate through the outlet pathway 137. Where the fluid pressure in the inlet pathway 132 is greater than the fluid pressure through the outlet pathway 137, this is an indication that the flow rate through the inlet pathway 132 is greater than the flow rate through the outlet pathway 137. The system of fluid pathways may include one or more damping mechanisms for dampening any extreme fluctuations in pressure within the fluid pathways.

Figure 3:
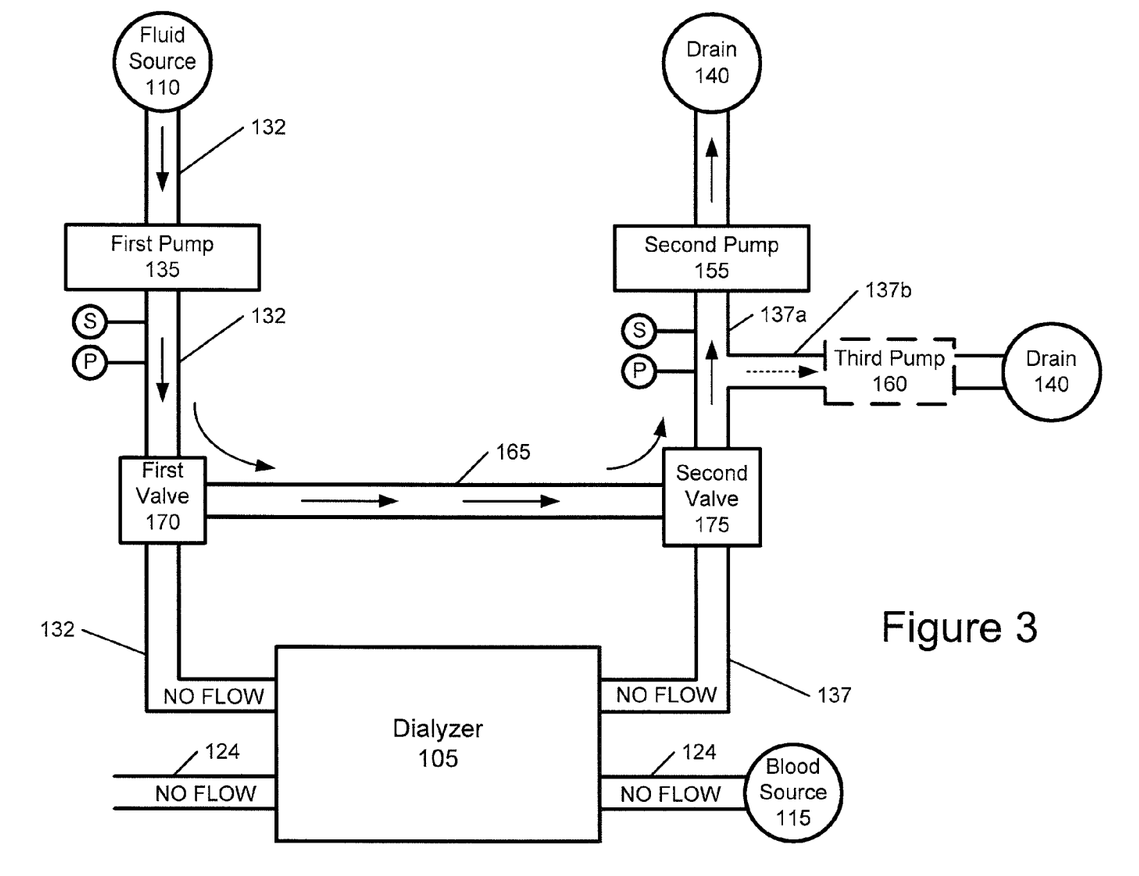
FIG. 3 shows a schematic representation of the system running in a calibration mode.

In the latter two situations, the pump rate of the third pump 160 may be adjusted in response to a pressure differential between the inlet and outlet pathways such as in a calibration procedure, to achieve a balanced flow rate between the inlet pathway 132 and outlet pathway 137. The calibration procedure may optionally be performed with the system in a calibration mode such that the first and second valves are set to cause fluid to flow through the bypass pathway 165 and bypass the dialyzer 105, as represented in FIG. 3 and described in more detail below. When the calibration procedure is performed by bypassing the dialyzer 105 and a pressure differential is detected between the inlet and outlet pathways, the flow of the third pump 160 may be appropriately adjusted 'on the fly' to increase or decrease the third pump's speed to achieve the desired flow rate in the outlet pathway 137 without having to turn the pump on or off. In this regard, the pressure sensors S and the three pumps, as well as the valves 175, may be connected in a closed loop control system to achieve automatic balancing of the flow rates.

In another embodiment, a balanced flow rate between the inlet pathway 132 and the outlet pathway 137 is achieved in theory at least by the first pump 135 and the second pump 155 operating at the same pump rate to achieve equal flow rates through the inlet pathway 132 and outlet pathway 137. Although it is theoretically possible to match the flow rates of the first pump 135 and the second pump 137, various factors may result in the actual fluid flow rate in the inlet pathway 132 differing from the actual fluid flow rate in the outlet pathway 137. The factors may include trapped air, hardware wear, and fluid leakage, which can cause the flow rates of the first and second pumps to diverge over time from a preset or desired value. Typical technologies in dialysis systems are unable to correct the flow balance for these types of factors.

Thus, there may come a time when a balanced flow rate cannot easily be achieved through use of the first and second pumps alone, and thus when there exists a need for correction to equalize the flow rates between the inlet pathway 132 and outlet pathway 137. Where the fluid flow rates are different, the third pump 160 can be used to correct the differing flow rates by being activated to pump fluid through the secondary outlet pathway 1137b at a rate that is equal to the delta between the fluid flow rate through the inlet pathway 132 and the fluid flow rate through the outlet pathway 137. The system is preferably configured such that the first pump 135 is prevented from pumping less fluid than the second pump 155 such that the first pump 135 always pumps at a higher rate than the second pump 155. The system preferably includes a control system that detects a condition where the first pump 135 inadvertently pumps at a slower rate than the second pump 155 and sets off an alarm or moves the system out of dialysis mode if such a situation occurs.

According to a flow rate correction process, the sensors S (FIG. 1) are used to measure the flow rates through the inlet pathway 132 and the outlet pathway 137. A comparison is performed between the flow rate through the inlet pathway 132 and the flow rate through the outlet pathway 137. Where the flow rates are different, the third pump 160 is activated from a de-activated state to cause fluid to flow into the secondary outlet pathway 137b at a rate selected to cause the overall flow rate in the outlet pathway 137 to be equal to the flow rate in the inlet pathway 132. A mechanism such as a servo mechanism may be used to adjust the stroke volume of the first pump 135 and/or the second pump 155 until balance of the flow rates is restored (as may be evidenced, for example, by the presence of the same fluid pressure in both the inlet pathway 132 and the outlet pathway 137).

As mentioned, the sensors S may be communicatively coupled to a control system and to the three pumps in a closed loop system. The control system includes hardware and/or software that automatically activates and/or deactivates the third pump 160 or adjusts the pump rate of the third pump 160 as needed in response to differences in detected flow rates from predetermined values or from each other, to equalize the flow rates between the inlet pathway 132 and outlet pathway 137. It should be appreciated that other measurements, such as fluid pressure in the inlet and outlet pathways, may be used to indirectly calculate the flow rates rather than directly measuring the flow rates. In this regard, the fluid pressures within the inlet pathway and the outlet pathway may be measured for any detectable change in pressure from a predetermined value or from each other. The flow pathways may be adapted to be essentially non-compliant so that a small difference in the flow rates of the first pump 135 and the second pump 155 will cause a rapid pressure change either negative or positive in magnitude.

The system may initially and/or periodically run in a calibration mode (sometimes also referred to as a UF checking mode) wherein a fluid (which may or may not be dialysate) is flowed through the flow pathways with the first valve 170 and second valve 137 set to the "bypass setting" such that fluid flowing through the system bypasses the dialyzer 105 via the bypass pathway 165. FIG. 3 shows a schematic representation of the system running in such a calibration mode where the dialyzer 105 is bypassed. In the embodiment where the system utilizes all three pumps in an active state substantially continuously throughout the hemodialysis procedure, the first and second pumps are initially deliberately set to achieve unbalanced flow rates. The sensors S in the flow pathway are then used to measure the fluid flow rate or pressure through the inlet pathway and the fluid flow rate or pressure through the outlet pathway. The third pump 160 is then set at a pump speed that achieves a substantially balanced flow rate between the inlet pathway 132 and outlet pathway 137.

In the other embodiment, the first pump 135 and second pump 155 are initially set to achieve equal flow rates without necessarily requiring the assistance of the third pump 160, which is initially inactive. The sensors S in the flow pathway are then used to measure the fluid flow rate through the inlet pathway and the fluid flow rate through the outlet pathway. Where the fluid flow rates are equal, the third pump 160 remains inactive. However, where the fluid flow rates are not equal, the third pump 160 is run at a rate that compensates for the discrepancy in flow rates between the inlet pathway 132 and outlet pathway 137. As mentioned, the third pump 160 may operate in a closed-loop relationship with the flow rate sensors and/or the pressure sensors. FIG. 3 shows the third pump 160 in phantom lines to represent the third pump may or may not be activated depending on whether there is a flow rate differential between the inlet pathway 132 and outlet pathway 137. The calibration procedure that does not require activating and de-activating the third pump is preferred as the system may run more efficiently when all three pumps are continuously operating.

After the calibration procedure is completed, the valves 170 and 175 may be set to the "dialysis setting" such that fluid flows from the source 110, through the inlet pathway 132, into the dialyzer 105, out of the dialyzer, and into the outlet pathway 137 from the dialyzer 105. When configured as such, the system can be used for dialysis by flowing dialysate into and out of the dialyzer 105 via the inlet and outlet pathways, and by also by flowing blood into and out of the dialyzer via the blood flow pathway 124. During dialysis, the previously described calibration procedure may be periodically repeated, such as at predetermined intervals, to ensure that the flow rates of the inlet and outlet pathways remain within desired ranges.

In an embodiment, calibration is run only at the beginning of a dialysis session. In a more preferred embodiment, calibration is run periodically during the dialysis session, to ensure that the desired flow balance is maintained throughout the session. The control system can cycle the valves 170 and 175 controlling incoming flow stream between the dialysis setting and the bypass setting and run the calibration steps without additional interruptions to the dialysis session. During the calibration process, when the dialysate fluid bypasses the dialyzer 105, dialysis of the blood that passes through the dialyzer during that period of time is unhampered due to no fresh dialysate being provided to the dialyzer 105, though the blood may cool slightly. As long as the calibration step can be conducted over a relatively short period of time relative to the time between calibrations, the calibration has no material effect on the quality of dialysis being provided to the patient. In an embodiment, the dialysis system can be cycled between calibration for one minute followed by 60 minutes of dialysate being delivered through the dialyzer. In another embodiment, the dialysis system can be cycled between calibration for 30 seconds followed by 120 minutes of dialysate being delivered through the dialyzer. Various different cycle times between calibration and dialysis may be chosen based on how frequently the system's calibration is to be verified and/or adjusted. If no adjustment to any of the pumps is necessary during calibration, the calibration step may be concluded in a much shorter period of time than 30-seconds, for example 5-10 seconds.

Figure 4:
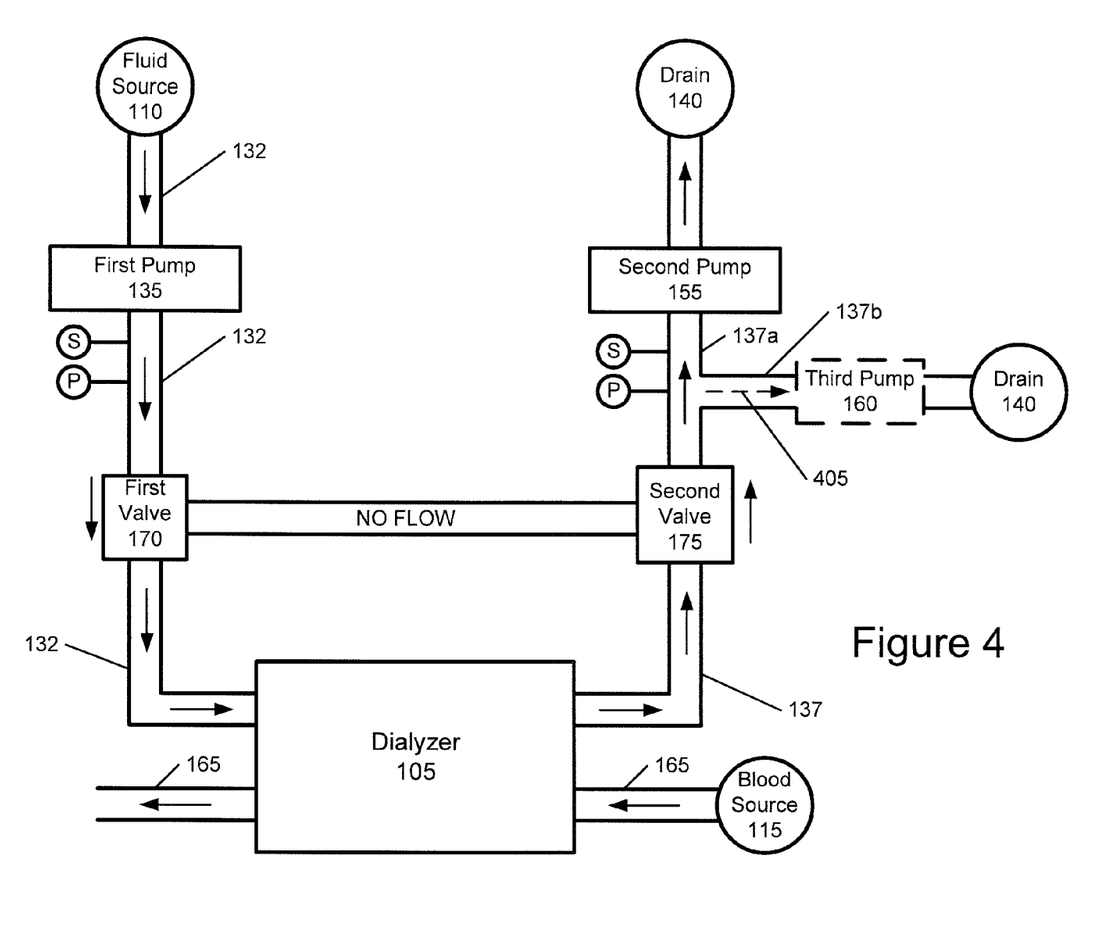
FIG. 4 shows a schematic representation of the system running in a dialysis mode.

FIG. 4 schematically shows the system running in a dialysis mode. The third pump 160 and the flow arrow 405 through the secondary outlet pathway 137b are shown in phantom lines to indicate that the third pump 160 may or may not be active while the system is in dialysis mode. The third pump 160 may be active in the situation where the third pump 160 is needed to equalize the flow rates between the inlet pathway and outlet pathways. Or, the flow rates of the inlet and outlet pathways may be equal without the assistance of the third pump 160, in which case the third pump 160 remains inactive.

Operation of Pumps to Achieve Ultrafiltration

The dialysis system achieves ultrafiltration in the situation where the flow rate through the inlet pathway 132 differs from the flow rate through the outlet pathway 137 such that there is an unbalanced flow rate across the dialyzer. Where the flow rate through the outlet pathway 137 is greater than the flow rate through the inlet pathway 132, the dialyzer 105 pulls fluid from the blood across the semipermeable membrane by a convective process in order to compensate for the unbalanced flow rate. In an embodiment, the system utilizes all three pumps substantially continuously throughout the procedure and the pump rate of the third pump 160 is adjusted to achieve a desired flow rate differential between the inlet pathway 132 and the outlet pathway 137 to perform ultrafiltration. That is, the first pump 135, second pump 155, and third pump 160 are all active with the first and second pumps operating at different pump rates. The third pump is then operated at a pump rate that intentionally achieves a desired imbalance of flow rates between the inlet pathway 132 and the outlet pathway 136 sufficient to cause ultrafiltration.

For example, to achieve the removal of fluid at a rate 10 ml/min from the blood stream, the first pump 135 is set to provide a flow rate of 100 ml/min through the inlet pathway 132 and the second pump 155 is deliberately set out of balance with the first pump 135, to provide, for example, a flow rate of only 80 ml/min. The third pump 160 is then set to provide a flow rate of 30 ml/min such that the second and third pumps collectively provide a flow rate of 110 ml/min through the outlet pathway 137. With a flow rate of 100 ml/min through the inlet pathway 132 and a flow rate of 110 ml/min through the outlet pathway, the dialyzer 105 compensates for the 10 ml/min flow rate differential by transferring 10 ml/min of fluid from the blood stream into the dialysate.

In another example, to achieve the addition of fluid at a flow rate of 10 ml/min into the blood stream, the first pump 135 is set to provide a flow rate of 100 ml/min through the inlet pathway 132 and the second pump 155 is again deliberately set out of balance with the first pump 135, to provide, for example, a flow rate of only 80 ml/min. The third pump 160 is then set to provide a flow rate of only 10 ml/min such that the second and third pumps collectively provide a flow rate of 90 ml/min through the outlet pathway 137. With a flow rate of 100 ml/min through the inlet pathway 132 and a flow rate of 90 ml/min through the outlet pathway, there is a transfer of 10 ml/min from the dialysate into the blood stream in order to compensate for the flow rate differential. It should be appreciated that the flow rate values in the preceding examples and following examples are only for purpose of example and that the actual flow rates as well as the relative flow rates can vary to achieve a desired level of ultrafiltration or reverse ultrafiltration.

The speed of the third pump 160 can be varied to selectively vary an amount of ultrafiltration. For example, if it is determined that the ultrafiltration is greater than desired when pulling fluid out of the blood, for example, the pump speed of the third pump 160 can be slowed down, reducing the amount of extra fluid that the third pump 160 draws out of the dialyzer. Where the ultrafiltration is not great enough when compared against a desired predetermined value, the pump speed of the third pump 160 may be increased in the case where fluid is being pulled out of the blood into the dialysate, for example, to draw an even greater amount of fluid out of the dialyzer and, hence, the blood.

In another embodiment, the third pump 160 may be coupled to a source of fluid such that the third pump 160 outputs extra fluid into the flow pathway via the secondary outlet pathway 137b, such as in the embodiment of FIG. 1B. The extra fluid introduced into the flow pathway is transferred across the semi-permeable membrane 215 into the blood.

Operation of Pumps to Achieve Hemodiafiltration

The dialysis system is configured to achieve hemodiafiltration by oscillating the speed of the third pump between (1) a first speed such that the second and third pump collectively achieve a flow rate through the outlet pathway that is greater than the flow rate through the inlet pathway; and (2) a second speed such that the second and third pump collectively achieve a flow rate through the outlet pathway that is less than the flow rate through the inlet pathway. In this manner, the third pump 160 can be used to intermittently alternate the flow rate differential between a state where the dialyzer 105 pulls fluid from the blood stream into the dialysate and a state where the dialyzer 105 pushes fluid from the dialysate into the blood stream. Over a predetermined span of time, there should be a zero net loss (or substantially a zero net loss) of fluid from the blood and a zero net gain (or substantially a zero net gain) of fluid into the blood for the process of hemodiafiltration. However, during that span of time, the dialyzer 105 periodically transfers fluid into the blood from the dialysate and periodically transfers fluid out of the blood into the dialysate. If ultrafiltration is desired to be performed at the same time as the hemodiafiltration, then the pumps can be operated in such a way so that in addition to the cycling of fluid into and out of the blood over time, there also occurs a net gain or loss of fluid to or from the blood over a predetermined span of time.

For example over an exemplary time span of ten minutes, the first pump 135 is set to provide a flow rate of 100 ml/min through the inlet pathway 132 and the second pump 155 is again deliberately set out of balance with the first pump 135, to provide, for example, a flow rate of only 80 ml/min. The speed of pump 160 can be cycled between a rate of 10 ml/min for a period of 30 seconds and 30 ml/min for a period of 30 seconds. During the periods when the speed of the third pump 160 is at a rate of 10 ml/min, the total flow rate through the outlet pathway 137 is 90 ml/min with the flow rate through the inlet pathway 132 at 100 ml/min, resulting in an unbalanced flow rate that causes the dialyzer 105 to transfer 10 ml/min of fluid into the blood stream. During the periods when the speed of the third pump 160 is at a rate of 30 ml/min, the total flow rate through the outlet pathway 137 is 110 ml/min with the flow rate through the inlet pathway 132 at 100 ml/min, resulting in an unbalanced flow rate that causes the dialyzer 105 to transfer 10 ml/min of fluid from the blood stream into dialysate. Over the span of ten minutes with alternating periods of 30 seconds as described above, there is a net balanced flow rate of 100 ml/min across the dialyzer without any net addition or subtraction of fluid from the blood. This serves the purpose of passing fluid to the blood across the membrane and then fluid from the blood to the dialysate across the membrane to achieve hemodiafiltration of the blood and increases the removal of large-molecular waste products that would not otherwise be effectively dialyzed. In this way, operation of the three or more-pump system can achieve all of hemodialysis, ultrafiltration and hemodiafiltration through how the speeds of the first, second, and third pumps are controlled. This type of operation has heretofore not been possible in other dialysis systems.

In another embodiment, shown in FIG. 1B, the third pump is located on the inlet flow side of the dialyzer instead of on the outlet flow path, such that the first and third pumps collectively achieve the desired inlet flow rate and the second pump achieves the desired outlet flow rate to perform one or more of hemodialysis, ultrafiltration and hemodiafiltration.

Between dialysis treatments, the flow pathways may be rinsed and/or disinfected. A rinse fluid, such as, but not limited to disinfectant solution and water, is routed through the flow pathways while the valves are in the bypass setting. During rinse mode, the third pump 160 may or may not be operated with the first pump 135 and second pump 155 to achieve fluid flow through the system.

Control of Flow Rates Using Pulsatile Pumps

In embodiments wherein the flow through flow pathways has a pulsatile nature, such as might be produced by certain types of pumps, the inherently high sensitivity of the methods described above might provide a challenge for controlling the flow rate as the small diameter and largely non-compliant flow pathways coupled with the pulsatile nature of the flow may make it difficult to measure pressures and pressure change rates sufficient to control the flow during dialysis.

In an embodiment, the pulsatile pressure signals present in a pulsatile flow configuration may be filtered out using appropriate signal conditioning. But the small volume and rigid flow pathways might cause too rapid of a pressure shift, quickly driving the pressure magnitude beyond the range of the pressure sensors. This may be particularly true for large, temporary mismatches associated with air being present in the flow pathways.

Figure 5:
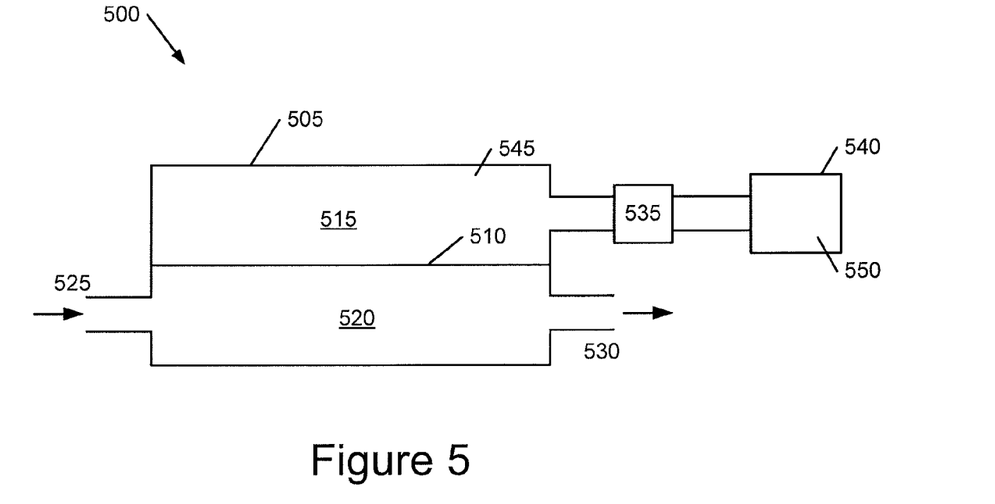
FIG. 5 is a cross-sectional view of a compliance control device.

FIG. 5 is a cross-sectional view of a compliance control device 500 that may be positioned in fluid communication with the flow pathways of the system. The device 500 is adapted to smooth out the pulsatile nature of the flow. The compliance control device 500 comprises a chamber 505 divided by a compliant diaphragm 510 defining a first chamber 515 and a second chamber 520. The first chamber 505 comprises a first chamber inlet 525 and a first chamber outlet 530 adapted for fluid communication with the flow pathways of the system. The second chamber 520 is in fluid communication with a control valve 535 and air plenum 540, wherein a non-compliant fluid 545, such as, but not limited to an inert liquid or gel, is disposed in the second chamber 520 and a compliant gas 550 is disposed in the air plenum 540.

When the dialysis system is performing hemodialysis, the control valve 535 may be closed restricting the flow of the non-compliant fluid 545 to the second chamber 520 creating a substantially non-compliant flow circuit as the compliant diaphragm 510 is restricted from complying (elastically deforming) against the now relatively rigid non-compliant fluid 545.

During calibration of the dialysis system, the control valve 535 may be opened, allowing the non-compliant fluid 545 to react with the gas 550 in the air plenum in reaction to pressure transients of the fluid in the pathway acting against the diaphragm 510. The diaphragm 510 moves in response to the pressure change and the gas 550 in the air plenum tends to moderate and smooth the pressure changes, allowing for a more precise pressure detection during calibration for flow compensation by the third pump 160.

Figure 6:
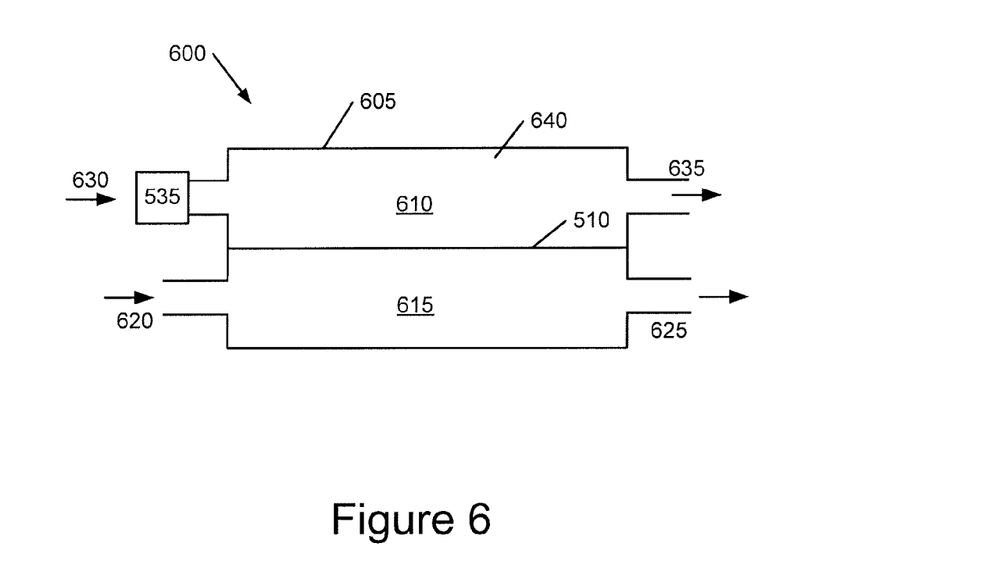
FIG. 6 is a cross-sectional view of another embodiment of a compliance control device.

FIG. 6 is a cross-sectional view of another compliance control device 600 adapted for fluid communication with the flow pathways of the system and adapted to smooth out the pulsatile nature of the flow such as during calibration. The compliance control device 600 comprises a chamber 605 divided by a compliant diaphragm 510 defining a first chamber 610 and a second chamber 615. The first chamber 610 comprises a first chamber inlet 620 and a first chamber outlet 625 adapted for fluid communication with the flow pathways of the system. The second chamber 615 comprises a second chamber inlet 630 and a second chamber outlet 635 adapted for fluid communication with a source of non-pulsatile flow of substantially non-compliant fluid 640. The fluid flow into the second chamber inlet 630 is controlled by a control valve 535 and the second chamber outlet 635 is in fluid communication with a drain.

During hemodialysis operation of the system, the control valve 535 is opened, allowing the flow of non-compliant fluid 640 to flow into the second chamber 615 and against the diaphragm 510 which restricts the movement of the diaphragm 510 and therefore creates a substantially non-compliant flow circuit. During calibration of the system, the control valve 535 is closed, restricting the flow of the non-compliant fluid 640 into the second chamber 615 with the non-compliant fluid 640 left in the second chamber 615 free to flow to the drain. Without the flow of non-compliant fluid 640 reacting against the diaphragm 510 and the remaining fluid 640 in the second chamber 615 free to drain, the fluid can react against the diaphragm 510 unconstrained by the non-compliant fluid 640. The diaphragm 510 elastically moves in response to any pressure change in the flow circuit moderating and smoothing the pressure change, allowing for a more precise pressure detection in the flow pathways for flow compensation by the third pump 160.

It is appreciated that the compliance control devices 500 and 600, such as provided in FIGS. 5 and 6, can be placed in fluid communication at any location in the flow pathways of the system such as upstream of the first valve 170 and downstream of the second valve 175, suitable for a particular purpose.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

The invention claimed is:

1. A method of performing dialysis, comprising:
operating a first pump to pump dialysate at a first flow rate through a fluid inlet pathway into a dialyzer;
operating a second pump to pump the dialysate through a fluid outlet pathway out of the dialyzer;
operating a third pump to pump the dialysate through the fluid outlet pathway in cooperation with the second pump, wherein the second and third pumps cooperate to collectively achieve a second flow rate through the fluid outlet pathway from the dialyzer;
pumping blood through the dialyzer in communication with the dialysate such that the dialyzer dialyzes the blood;
varying the pumping speed of at least one of the first pump, second pump and third pump to allow the dialyzer to individually perform hemodialysis, ultrafiltration and hemodiafiltration based on relative pumping speeds between the first pump, second pump and third pump;

calibrating periodically the first pump, second pump, and third pump by diverting a fluid traveling from the fluid inlet pathway to the fluid outlet pathway through a bypass conduit such that the fluid bypasses the dialyzer.

2. The method of claim 1, wherein the first, second and third pumps operate to maintain balance between the fluid flow rates in the inlet pathway and outlet pathway such that substantially no fluid is added to or removed from the blood during operation.

3. The method of claim 1, wherein the first, second and third pumps operate to maintain balance between the fluid flow rates in the inlet pathway and outlet pathway such that a desired rate of fluid addition to the blood during operation is achieved.

4. The method of claim 1, wherein the first, second and third pumps operate to maintain balance between the fluid flow rates in the inlet pathway and outlet pathway such that a desired amount of fluid is removed from the blood during operation.

5. The method of claim 1, wherein the first, second and third pumps operate to maintain balance between the fluid flow rates in the inlet pathway and outlet pathway such that a desired amount of fluid is added to the blood during a time span of operation.

6. The method of claim 1, wherein the first, second and third pumps operate to maintain balance between the fluid flow rates in the inlet pathway and outlet pathway such that an amount of fluid is removed to the blood during a time span of operation.

7. The method of claim 1, wherein the first, second and third pumps operate to achieve a desired level of hemodiafiltration by cycling the third pump between a lower speed and a higher speed substantially without a net addition of fluid to the blood.

8. The method of claim 1, wherein the first, second and third pumps operate to achieve a desired level of hemodiafiltration and a desired rate of fluid addition to the blood by cycling the third pump between a lower speed and a higher speed.

9. The method of claim 1, wherein the first, second and third pumps operate to achieve a desired level of hemodiafiltration and a desired rate of fluid removal from the blood by cycling the third pump between a lower speed and a higher speed.

10. A method of performing dialysis, comprising:
providing a dialysis system having an inlet conduit through which fluid flows in an inward direction toward a dialyzer and an outlet conduit through which fluid flows in an outward direction from the dialyzer;
pumping fluid through the inlet conduit using a first pump;
pumping fluid through the outlet conduit using a second pump; and
using a third pump to supplement the pumping of the second pump through the outlet conduit;
varying the pumping speed of at least one of the first pump, second pump and third pump to allow the dialyzer to individually perform hemodialysis, ultrafiltration and hemodiafiltration based on relative pumping speeds between the first pump, second pump and third pump;
calibrating periodically the first pump, second pump, and third pump by diverting fluid traveling from the inlet conduit to the outlet conduit through a bypass conduit such that fluid bypasses the dialyzer.

11. A method as in claim 10, further comprising measuring a first fluid pressure in the inlet conduit and a second fluid pressure in the outlet conduit and adjusting a pump speed of the third pump based on the first and second fluid pressures.

12. A method as in claim 10, wherein adjusting a pump speed of the third pump based on the first and second fluid pressures comprises adjusting the pump speed of the third pump based on a pressure differential between the first fluid pressure and the second fluid pressure.

13. A method as in claim 10, wherein the fluid is dialysate and further comprising pumping blood through the dialyzer to achieve dialysis of the blood, and further comprising operating the third pump in a manner such that no fluid is added or removed from the blood during dialysis.

14. A method as in claim 10, wherein the fluid is dialysate and further comprising pumping blood through the dialyzer to achieve dialysis of the blood, and further comprising operating the third pump in a manner such that fluid is added to the blood from the dialysate during dialysis.

15. A method as in claim 10, wherein the fluid is dialysate and further comprising pumping blood through the dialyzer to achieve dialysis of the blood, and further comprising operating the third pump in a manner such that fluid is removed from dialysate into the blood during dialysis.

16. A method as in claim 10, wherein the fluid is dialysate and further comprising pumping blood through the dialyzer to achieve dialysis of the blood, and further comprising operating the third pump in a manner such that fluid is removed from the blood into the dialysate, and then operating the third pump in a manner such that fluid is added into the blood from the dialysate.

17. A method as in claim 16, wherein there is substantially no net gain of fluid into the blood and no loss of fluid from the blood over a predetermined span of time.

18. A method as in claim 10, wherein a first valve and a second valve control the flow of fluid through the bypass conduit.

19. The method of claim 1, wherein the first pump is set to provide a flow rate of approximately 100 ml/min, the second pump is set to provide a flow rate of approximately 80 ml/min and the third pump is set to provide a flow rate of approximately 30 ml/min.

20. The method of claim 19, wherein approximately 10 ml/min of fluid from the blood is transferred into the dialysate.

21. The method of claim 1, wherein the first pump is set to provide a flow rate of approximately 100 ml/min, the second pump is set to provide a flow rate of approximately 80 ml/min and the third pump is set to provide a flow rate of approximately 10 ml/min.

22. The method of claim 21, wherein approximately 10 ml/min of dialysate is transferred into the blood.

* * * * *